United States Patent
Gers-Barlag et al.

(10) Patent No.: US 7,186,415 B1
(45) Date of Patent: Mar. 6, 2007

(54) FINELY DISPERSED EMULSIFIER-FREE SYSTEMS OF THE OIL-IN-WATER AND WATER-IN-OIL TYPE, CONTAINING BORON NITRIDE

(75) Inventors: Heinrich Gers-Barlag, Kummerfeld (DE); Anja Müller, Rümpel (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/744,642

(22) PCT Filed: Jul. 22, 1999

(86) PCT No.: PCT/EP99/05243

§ 371 (c)(1),
(2), (4) Date: Jan. 26, 2001

(87) PCT Pub. No.: WO00/07549

PCT Pub. Date: Feb. 17, 2000

(30) Foreign Application Priority Data

Aug. 1, 1998 (DE) ................................ 198 34 820

(51) Int. Cl.
*A61K 6/00* (2006.01)
*A61K 9/70* (2006.01)

(52) U.S. Cl. .................. 424/401; 424/59; 424/455; 424/78.03

(58) Field of Classification Search .............. 424/657, 424/59, 455, 401, 78.03
See application file for complete search history.

(56) References Cited

U.S. PATENT DOCUMENTS

| | | | |
|---|---|---|---|
| 4,898,913 A | 2/1990 | Ziemelis et al. | |
| 5,246,780 A | 9/1993 | Farer et al. | |
| 5,486,233 A * | 1/1996 | Mitchell et al. ............ | 106/416 |
| 5,643,555 A | 7/1997 | Collin et al. | |
| 5,725,844 A * | 3/1998 | Gers-Barlag et al. ........ | 424/59 |
| 5,788,952 A * | 8/1998 | Gers-Barlag et al. ........ | 424/59 |
| 5,833,951 A | 11/1998 | Arzt et al. | |
| 6,004,567 A | 12/1999 | Marchi-Lemann et al. | |
| 6,197,282 B1 * | 3/2001 | Oshima et al. .............. | 424/59 |
| 6,592,883 B1 * | 7/2003 | Gers-Barlag et al. ....... | 424/401 |
| 6,703,032 B2 * | 3/2004 | Gers-Barlag et al. ....... | 424/401 |

FOREIGN PATENT DOCUMENTS

| | | | |
|---|---|---|---|
| DE | 43 03 983 A1 | | 8/1994 |
| DE | 4425268 | | 1/1996 |
| EP | 0686391 | | 12/1995 |
| EP | 0 796 612 A1 | | 9/1997 |
| FR | 2 746 301 A1 | | 9/1997 |
| JP | 3-017011 | | 1/1991 |
| JP | 03-017011 | | 9/1992 |
| JP | 7-101828 | | 4/1995 |
| JP | 07-101828 | | 1/1996 |
| JP | 08-113514 | * | 5/1996 |
| JP | 08-113514 | | 11/1997 |
| JP | 10-017785 | | 1/1998 |
| JP | 10017785 | | 1/1998 |
| WO | WO 93/04668 | | 3/1993 |
| WO | WO97/45097 | * | 12/1997 |
| WO | WO 00/07549 | | 2/2000 |

OTHER PUBLICATIONS

Introini, C.: "Nitruro di Boro. Nuova Materia Prima" Cosmet. Toiletries, Ed. Ital., Bd 18, Nr. 3, 1997, Seiten 26-27, 30-32, XP000853905.

Intronin, C.: "Nitruro di Boro. Nuevo ingredient nei prodotti per il corpo e nei solari" Cosmet. Toiletries, Ed. Ital., Bd. 18, Nr. 2, 1997, Seiten 71, 73, 75-76, XP000853904.

English Language Abstract of JP 10-017785.
English Language Abstract of JP 3-017011.
English Language Abstract of JP 7-101828.
English Language Translation and English Language Abstract of JP 8-113514.
JP 91-069027/ 10.

* cited by examiner

*Primary Examiner*—Sreeni Padmanabhan
*Assistant Examiner*—Gina C. Yu
(74) *Attorney, Agent, or Firm*—Greenblum & Bernstein, P.L.C.

(57) ABSTRACT

Cosmetic or dermatological preparations, which are finely dispersed systems of the oil-in-water or water-in-oil type, comprising
1. an oil phase,
2. an aqueous phase,
3. boron nitride which has both hydrophilic and lipophilic properties, i.e. has amphiphilic character, and thus positions itself at the water/oil interface, and
4. at most 0.5% by weight of one or more emulsifiers and also optionally comprising further cosmetic or pharmaceutical auxiliaries, additives and/or active ingredients.

20 Claims, No Drawings

FINELY DISPERSED EMULSIFIER-FREE SYSTEMS OF THE OIL-IN-WATER AND WATER-IN-OIL TYPE, CONTAINING BORON NITRIDE

DESCRIPTION

This application is a 371 of PCT/EP99/05243, which was filed on Jul. 22, 1999.

The present invention relates to emulsifier-free finely dispersed systems of the oil-in-water and water-in-oil type, preferably as cosmetic or dermatological preparations.

Emulsions are generally taken to mean heterogeneous systems which consist of two liquids which are immiscible or have only limited miscibility with one another, which are usually referred to as phases. In an emulsion, one of the two liquids is dispersed in the form of very fine droplets in the other liquid.

If the two liquids are water and oil and if oil droplets are finely dispersed in water, then this is an oil-in-water emulsion (O/W emulsion, e.g. milk). The basic character of a O/W emulsion is defined by the water. In a water-in-oil emulsion (W/O emulsion, e.g. butter), the principle is reversed, the base character here being determined by the oil.

In order to achieve permanent dispersion of one liquid in another, emulsions in the traditional sense require the addition of an interface-active ingredient (emulsifier). Emulsifiers have an amphiphilic molecular structure, consisting of a polar (hydrophilic) and a nonpolar (lipophilic) molecular moiety, which are spatially separate from one another. In simple emulsions, finely dispersed droplets of one phase, surrounded by an emulsifier shell, (water droplets in W/O emulsions or lipid vesicles in O/W emulsions) are present in the second phase. Emulsifiers lower the interfacial tension between the phases by positioning themselves at the interface between the two liquids. At the phase boundary, they form oil/water interfacial films, which prevent irreversible coalescence of the droplets. Emulsions are frequently stabilized using emulsifier mixtures.

Traditional emulsifiers can, depending on their hydrophilic molecular moiety, be divided into ionic (anionic, cationic and amphoteric) and nonionic:

The most well known example of an anionic emulsifier is soap, which is usually the term used for the water-soluble sodium salts or potassium salts of saturated or unsaturated higher fatty acids.

Important examples of cationic emulsifiers are quaternary ammonium compounds.

The hydrophilic molecular moiety of nonionic emulsifiers frequently consists of glycerol, polyglycerol, sorbitans, carbohydrates and polyoxyethylene glycols, and, in most cases, is linked to the lipophilic molecular moiety via ester and ether bonds. The lipophilic molecular moiety usually consists of fatty alcohols, fatty acids or isofatty acids.

By varying the structure and the size of the polar and nonpolar molecular moiety, the lipophilicity and hydrophilicity of the emulsifiers can be varied within wide limits.

A decisive factor for the stability of an emulsion is the correct choice of emulsifiers. The characteristics of all substances present in the system are to be taken into consideration. In the case of, for example, skin care emulsions, polar oil components and, for example, UV filters lead to instability. As well as the emulsifiers, therefore, other stabilizers are also used which, for example, increase the viscosity of the emulsion and/or act as a protective colloid.

Emulsions are an important type of product in the field of cosmetic and/or dermatological preparations.

Cosmetic preparations are essentially used for skin care. The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes). If this function becomes impaired, increased resorption of toxic or allergenic substances or infection by microorganisms may result, leading to toxic or allergic skin reactions.

Another aim of skin care is to compensate for the loss by the skin of grease and water caused by daily washing. This is particularly important if the natural regeneration ability in inadequate. Furthermore, skin care products should protect against environmental influences, in particular against sun and wind, and delay skin ageing.

Cosmetic preparations are also used as deodorants. Such formulations are used to control body odour which is produced when fresh sweat, which is in itself odourless, is decomposed by microorganisms.

Medicinal topical compositions usually comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Regulation, Foods and Drugs Act).

The use of customary emulsifiers in cosmetic or dermatological preparations is in itself acceptable. Nevertheless, emulsifiers, like ultimately any chemical substance, may in certain circumstances cause allergic reactions or reactions based on oversensitivity of the user.

For example, it is known that certain light dermatoses are triggered by certain emulsifiers, but also by a variety of fats and simultaneous exposure to sunlight. Such light dermatoses are also-called "Mallorca acne". There has thus been no lack of attempts to reduce the amount of customary emulsifiers to a minimum, in the ideal case even to zero.

A reduction in the required amount of emulsifier can, for example, be achieved by taking advantage of the fact that very finely divided solid particles have an additional stabilizing action. The solid substance accumulates at the oil/water phase boundary in the form of a layer, as a result of which coalescence of the dispersed phases is prevented. It is not the chemical properties of the solid particles which are of fundamental importance here, but the surface properties.

Around 1910, Pickering prepared paraffin/water emulsions which were stabilized merely by the addition of various solids, such as basic copper sulphate, basic iron sulphate or other metal sulphates. This type of emulsion is thus also referred to as a Pickering emulsion. For this type of emulsion, Pickering postulated the following conditions:

(1) The solid particles are only suitable for stabilization if they are significantly smaller than the droplets of the inner phase and do not have a tendency to form agglomerates.

(2) An important property of an emulsion-stabilizing solid is also its wettability. I.e. in order to stabilize an O/W emulsion, the solid has, for example, to be more readily wettable by water than by oil.

The original forms of Pickering emulsions initially surfaced, as it were, as undesired secondary effects in a variety of industrial processes, such as, for example, in secondary oil recovery, the extraction of bitumen from tar sand and other separation processes involving two immiscible liquids and fine, dispersed solid particles. These are generally W/O emulsions which are stabilized by mineral solids. Accordingly, investigation of corresponding systems, such as, for example, the oil/water/soot or oil/water/slate dust systems was initially the focus of research activity.

Basic experiments have been shown that one characteristic of a Pickering emulsion is that the solid particles are arranged at the interface between the two liquid phases where they form, as it were, a mechanical barrier against the mixing of the liquid droplets.

It is a relatively new technical development to use Pickering emulsions as a base for cosmetic or dermatological preparations.

One way of achieving solids stabilization in a cosmetic or dermatological preparation is, according to May-Alert (Pharmazie in unserer Zeit [Pharmacy in our time], Vol. 15, 1986, No. 1, 1–7) for example, to use emulsifier mixtures which contain both anionic and cationic surfactants. Since mixing anionic and cationic surfactants always produces precipitates of insoluble, electroneutral compounds, deliberate precipitation of these neutral surfactants in the oil/water interface makes it possible to achieve additional solids stabilization in the sense of a Pickering emulsion.

EP-A-0 668 391 describes water-in-oil emulsions which are free from surface-active ingredients and are stabilized only by solids. Stabilization is achieved here using spherical polyalkylsilsequioxane particles which have a diameter of from 100 nm up to 20 nm. According to the above, these emulsions can be referred to as Pickering emulsions.

In addition to the described Pickering emulsions, the prior art describes further emulsifier-free, finely dispersed cosmetic or dermatological preparations which are generally referred to as hydrodispersions. Hydrodispersions are dispersions of a liquid, semi-solid or solid internal (discontinuous) lipid phase in an outer aqueous (continuous) phase.

In the case of hydrodispersions of a liquid lipid phase in an outer aqueous phase, stability can be ensured, for example, by constructing, in the aqueous phase, a gel structure in which the lipid droplets are stably suspended. DE-A 44 25 268 describes stable finely dispersed, emulsifier-free cosmetic or dermatological preparations of the oil-in-water type, which, in addition to one oil phase and one water phase, comprise one or more thickeners from the group consisting of acrylic polymers, polysaccharides and alkyl ethers thereof, where these thickeners must not cause any lowering of the interfacial tension.

Using similar hydrodispersions as a basis, DE-A 43 03 983 discloses cosmetic or dermatological light protection formulations which are essentially free from emulsifiers, and which have inorganic micropigments incorporated into the lipid phase of the hydrodispersion, which act as UV filter substances.

The object of the present invention was to extend the prior art to include cosmetic or dermatological preparations in which it is not necessary to use any emulsifiers of a conventional type.

Surprisingly, this object is achieved by cosmetic or dermatological preparations which are finely dispersed systems of the oil-in-water or water-in-oil type, comprising
1. an oil phase,
2. an aqueous phase
3. boron nitride which has both hydrophilic and lipophilic properties, i.e. has amphiphilic character, and positions itself at the water/oil interface, and
4. at most 0.5% by weight of one or more emulsifiers and also optionally comprising further cosmetic or pharmaceutical auxiliaries, additives and/or active ingredients.

It is particularly advantageous according to the invention if the preparations comprise significantly less than 0.5% by weight of one or more emulsifiers or are even entirely emulsifier-free.

The preparations according to the invention are mixtures of oil or oil-soluble substances and water or water-soluble components, which are stabilized by adding boron nitride particles and which do not have to contain an emulsifier in the traditional sense. Stabilization is achieved by the boron nitride particles attaching themselves to the droplets of the disperse phase and forming, as it were, a mechanical barrier, which prevents coalescence of the droplets.

The preparations according to the invention are extremely satisfactory preparations in every respect, whose aqueous/fatty phase ratio can be varied within extraordinarily wide limits and, in addition, have the advantage over the prior art that large amounts of oils can be stably incorporated in water. It was also surprising that by following the teaching disclosed here as regards technical handling, it is possible to prepare water-in-oil Pickering emulsions and also oil-in-water Pickering emulsions.

For the purposes of the present invention, the boron nitrides listed below, for example, are advantageous:

| Trade name | available from |
|---|---|
| Boron Nitride Powder | Advanced Ceramics |
| Boron Nitride Powder | Sintec Keramik |
| Ceram Blanche | Kawasaki |
| HCST Boron Nitride | Stark |
| Très BN ® | Carborundum |
| Wacker-Bornitrid BNP | Wacker-Chemie |

It is advantageous to choose the average particle diameter of the boron nitride particles used to be less than 20 µm, particularly advantageously less than 15 µm.

Within the meaning of the present invention, Pickering emulsions are likewise advantageously stabilized by boron nitride particles which have been surface treated ("coated") to repel water, the intention being for the amphiphilic character to be simultaneously formed or retained.

An advantageous coating of the boron nitride particles consists of dimethylpolysiloxane (also: dimethicone), a mixture of completely methylated, linear siloxane polymers which have been terminally blocked with trimethylsiloxy units. The boron nitride particles treated with dimethicone and obtainable from Carborundum under the trade name Très BN® UHP 1106, for example, are advantageous.

Also advantageous is a coating of the boron nitride particles with polymethyl hydrogen siloxane, a linear polysiloxane, which is also referred to as methicone. Advantageous boron nitride particles treated with methicone are, for example, those obtainable from Carborundum under the trade name Très BN® UHP 1107.

It is also advantageous, but not obligatory, to combine the amphiphilic boron nitride particles according to the invention with further amphiphilic pigments which may optionally also contribute to the stabilization of the Pickering emulsions.

Such pigments are, for example, micronized inorganic pigments chosen from the group of amphiphilic metal oxides, in particular from the group consisting of titanium, dioxide, zinc oxide, silicon dioxide or silicates (e.g. talc), it being possible for the metal oxides to be present either individually or as a mixture. In this connection, it is essentially unimportant in which of the potentially naturally occurring modifications the amphiphilic metal oxides used are present.

It is advantageous to choose the average particle diameter of the pigments used for the combination with boron nitrides to be between 1 nm and 200 nm, particularly advantageously between 5 nm and 100 nm.

It is advantageous for the purposes of the present invention to combine the amphiphilic boron nitride particles according to the invention with untreated, virtually pure pigment particles, in particular with those which can also be used as dye in the food industry and/or as absorber of UV radiation in sunscreens. Examples of advantageous pigments are the zinc oxide pigments which are available from Merck and those which are available under the trade names Zinkoxid neutral from Haarmann & Reimer or NanoX from Harcros Chemical Group.

According to the invention, it is also advantageous to combine boron nitride particles with inorganic pigments which have been surface-treated (coated) to repel water, the intention being for an amphiphilic character of these pigments to be formed or retained. This surface-treatment may involve providing the pigments with a thin hydrophobic layer by processes known per se.

One such process, which is described below using titanium dioxide as an example, consists in, for example, producing the hydrophobic surface layer according to the following reaction

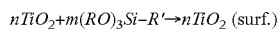

$n TiO_2 + m(RO)_3 Si-R' \rightarrow n TiO_2 \text{ (surf.)}$ n and m are stoichiometric parameters to be used as desired, and R and R' are the desired organic radicals. Particularly advantageous combination partners are $TiO_2$ pigments, for example those coated with aluminium stearate and available under the trade name MT 100 T from TAYCA.

Another advantageous coating of the combination partners consists of dimethylpolysiloxane (also: dimethicone), a mixture of completely methylated, linear siloxane polymers which have been terminally blocked with trimethylsiloxy units. The combination of boron nitrides with zinc oxide pigments which have been coated in this way is particularly advantageous for the purposes of the present invention.

It is also advantageous if the inorganic pigments used in addition to boron nitride have been coated with a mixture of dimethylpolysiloxane, in particular dimethylpolysiloxane having an average chain length of from 200 to 350 dimethylsiloxane units, and silica gel, which is also referred to as simethicone. It is particularly advantageous if the inorganic pigments have been additionally coated with aluminium hydroxide or hydrated aluminium oxide (also: alumina, CAS No.: 1333-84-2). Particularly advantageous combination partners are titanium dioxides which have been coated with simethicone and alumina, it also being possible for the coating to comprise water. One example thereof is the titanium dioxide obtainable under the trade name Eusolex T2000 from Merck.

Also advantageous for the purposes of the present invention is the combination of boron nitrides with a mixture of different inorganic, amphiphilic pigment types both within a crystal, for example as iron mixed oxide or talc (magnesium silicate), and also by mixing two or more metal oxide types within a preparation. Particularly advantageous combination partners are magnesium silicates, for example those obtainable under the trade name Talkum Micron from Grolmann.

The amphiphilic boron nitride particles according to the invention can also advantageously be combined with further pigments, for example with titanium dioxide pigments which have been coated with octylsilanol, and/or with silicon dioxide particles which have been surface-treated to repel water. Silicon dioxide particles which are suitable for the combination are, for example, spherical polyalkylsilsesquioxane particles, as mentioned in European Laid-Open Specification 0 686 391. Such polyalkylsilsesquioxane particles are, for example, obtainable under the trade names Aerosil R972 and Aerosil 200V from Degussa.

The amphiphilic boron nitride particles are further advantageously combined with microfine polymer particles which are present in the preparation in the form of solids. Favourable combination partners for the purposes of the present invention are, for example, polycarbonates, polyethers, polyethylene, polypropylene, polyvinyl chloride, polystyrene, polyamides, polyacrylates and the like.

Combination partners suitable according to the invention are, for example, microfine polyamide particles, in particular those obtainable under the trade name SP-500 from TORAY. Also advantageous are polyamide 6 (also: nylon 6) or polyamide 12 (also: nylon 12) particles. Polyamide 6 is the polyamide [poly(ε-caprolactam)] built up from ε-aminocaproic acid (6-aminohexanoic acid) or ε-caprolactam, and polyamide 12 is a poly(ε-laurolactam) of ε-laurolactam. Advantageous for the purposes of the present invention are, for example, Orgasol® 1002 (Polyamide 6) and Orgasol® 2002 (Polyamide 12) from ELF ATOCHEM.

Further advantageous microfine polymer particles which are suitable for the combination with the boron nitride particles according to the invention are microfine polymethacrylates. Such particles are available, for example, under the trade name POLYTRAP® from DOW CHEMICAL.

It is particularly advantageous, although not obligatory, if the microfine polymer particles used as combination partners have been surface-coated. This surface treatment can involve providing the polymer particles with a thin hydrophilic layer by processes known per se. Advantageous coatings consist, for example, of titanium dioxide ($TiO_2$), zirconium dioxide ($ZrO_2$) or else further polymers, such as, for example, polymethyl methacrylate. Particularly advantageous microfine polymer particles for the purposes of the present invention are, for example, those obtainable by the process described in U.S. Pat. No. 4,898,913 for the hydrophilic coating of hydrophobic polymer particles.

The average particle diameter of the microfine polymer particles used as combination partners is preferably chosen to be less than 100 μm, particularly advantageously to be less than 50 μm. Here, it is essentially unimportant in which form (platelets, rods, spherules etc.) the polymer particles used are present.

The amphiphilic boron nitride particles according to the invention are also preferably combined with amphiphilic modified polysaccharides which do not exhibit thickening properties.

Such amphiphilic polysaccharides are obtainable, for example, by reacting starch with mono-, bi- or polyfunctional reagents or oxidizing agents in reactions which proceed in a predominantly polymer-analogous manner.

These reactions are based essentially on modifications of the hydroxyl groups of the polyglucans by etherification, esterification or selective oxidation. This produces, for example, so-called starch ethers and starch esters of the general structural formula

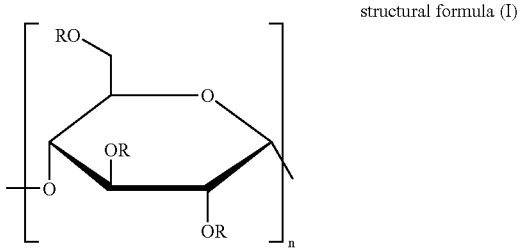

structural formula (I)

in which R can, for example, be a hydrogen and/or an alkyl and/or aralkyl radical (in the case of the starch ethers) or a hydrogen and/or an organic and/or inorganic acid radical (in the case of the starch esters). Starch ethers and starch esters are advantageous combination partners for the purposes of the present invention.

It is particularly advantageous to combine the boron nitride particles according to the invention with starch ethers, e.g. with those obtainable by etherifying starch with tetramethylolacetylenediurea and which are referred to as Amylum non mucilaginosum (nonswelling starch).

Also particularly advantageous is the combination of boron nitride particles according to the invention with starch esters and/or salts thereof, for example with sodium and/or aluminium salts of starch half-esters which have low degrees of substitution, in particular with sodium starch n-octenyl succinate of the structural formula (I), in which R is characterized by the following structure

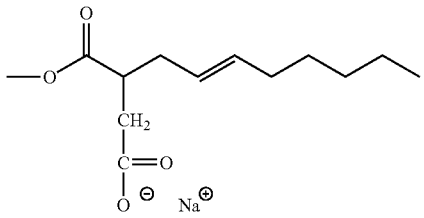

and which is obtainable e.g. under the trade name Amiogum® 23 from CERESTAR, and also with aluminium starch octenyl succinate, in particular with those available under the trade names Dry Flo® Elite LL and Dry Flo® PC from CERESTAR.

It is advantageous to choose the average particle diameter of the modified polysaccharides used for the combination with the amphiphilic boron nitride particles according to the invention to be less than 20 μm, particularly advantageously less than 15 μm.

The list of said modified polysaccharides which can be combined with the amphiphilic boron nitride particles is not of course intended to be limiting. Modified polysaccharides which are advantageous combination partners for the purposes of the present invention are obtainable by numerous methods, both chemical and physical in nature, which are known per se. For the preparation of such polysaccharides, novel methods are in principle also conceivable. In this connection, it is essential that the modified polysaccharides exhibit amphiphilic properties and that they do not have a thickening action.

In all of the above cases it is advantageous to choose the total concentration of all the pigments to be greater than 0.1% by weight, particularly advantageously between 0.1% and 30% by weight, based on the total weight of the preparations, where the concentration of boron nitride is to be chosen, for the purposes of the present invention, preferably from the range 0.1% by weight to 30% by weight, advantageously 0.5% by weight to 10% by weight, likewise based on the total weight of the preparations.

The Pickering emulsions according to the invention can be used as bases for cosmetic or dermatological formulations. These can have the customary composition and be used, for example, for the treatment and care of the skin, as lip care product, as deodorant and as make-up or make-up remover product in decorative cosmetics or as light protection preparation. For use, the cosmetic and dermatological preparations according to the invention are applied to the skin in sufficient amount in the manner customary for cosmetics.

Accordingly, for the purposes of the present invention, cosmetic or topical dermatological compositions may, depending on their structure, be used, for example, as skin-protection cream, cleansing milk, sunscreen lotion, nutrient cream, day or night cream, etc. Where appropriate, it is possible and advantageous to use the compositions according to the invention as bases for pharmaceutical formulations.

The cosmetic and dermatological preparations according to the invention may comprise cosmetic auxiliaries, as customarily used in such preparations, e.g. preservatives, bactericides, perfumes, antifoams, dyes, pigments which have a colouring effect, thickeners, plasticizers, moisturizing and/or moisture-retaining substances, fats, oils, waxes or other customary constituents of a cosmetic or dermatological formulation, such as alcohols, polyols, polymers, foam stabilizers, electrolytes, organic solvents or silicone derivatives.

A surprising property of the preparations according to the invention is that they are very good vehicles for cosmetic or dermatological active ingredients into the skin, advantageous active ingredients being antioxidants which are able to protect the skin against oxidative stress.

According to the invention, the preparations advantageously comprise one or more antioxidants. Antioxidants which are favourable, but nevertheless optional, are all antioxidants which are suitable or customary for cosmetic and/or dermatological applications. Here, it is advantageous to use antioxidants as the sole active ingredient class whenever, for example, a cosmetic or dermatological application is at the fore, such as e.g. the control of oxidative stressing of the skin. It is, however, also favourable to provide the stick preparations according to the invention with a content of one or more antioxidants whenever the preparations are to serve another purpose, e.g. as deodorants or sunscreens.

The antioxidants are particularly advantageously selected from the group consisting of amino acids (e.g. glycine, histidine, tyrosine, tryptophan) and their derivatives, imidazoles, (e.g. urocanic acid) and their derivatives, peptides, such as D,L-carnosine, D-carnosine, L-carnosine and their derivatives (e.g. anserine), carotenoids, carotenes (e.g. α-carotene, β-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and gylceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa-, hepta-thionine sulphoximines) in very low tolarated doses (e.g. pmol to µmol/kg), and also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and its derivatives, α-glycosylrutin, ferulic acid, furfurylideneglucitol, carnosine, butylated hydroxytoluene, butylated hydroxyanisole, nordihydroguaiac acid, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active ingredients which are suitable according to the invention.

The amount of the abovementioned antioxidants (one or more compounds) in the preparations according to the invention is preferably from 0.001 to 30% by weight, particularly preferably from 0.05 to 20% by weight, in particular 1–10% by weight, based on the total weight of the preparation.

If vitamin E and/or its derivatives are used as the antioxidant or antioxidants, their respective concentrations are advantageously chosen from the range of 0.001–10% by weight, based on the total weight of the formulation.

If vitamin A or vitamin A derivatives or carotenes or their derivatives are used as the antioxidant or antioxidants, their respective concentrations are advantageously chosen from the range of 0.001–10% by weight, based on the total weight of the formulation.

According to the invention, the active ingredients (one or more compounds) can also very advantageously be chosen from the group of lipophilic active ingredients, in particular from the following group:

Acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favourably vitamin $B_1$, vitamin $B_{12}$ and vitamin $D_1$, but also bisabolol, unsaturated fatty acids, namely the essential fatty acids (often also-called vitamin F), in particular gamma-linolenic acid, oleic acid, eicosapentaenoic acid, docosahexanoic acid and derivatives thereof, chloramphenicol, caffeine, prostaglandins, thymol, camphor, extracts or other products of vegetable and animal origin, e.g. evening primrose oil, borage oil or currant seed oil, fish oils, cod-liver oil or also ceramides and ceramide-like compounds and so on.

It is also advantageous to choose the active ingredients from the group of refatting substances, for example purcellin oil, Eucerit® and Neocerit®.

The list of said active ingredients or active ingredient combinations which can be used in the Pickering emulsions according to the invention is not of course intended to be limiting.

Cosmetic and dermatological preparations which are in the form of a sunscreen are also favourable. These preferably comprise at least one UV-A filter substance and/or at least one UV-B filter substance and/or at least one further inorganic pigment selected from the group consisting of the oxides of iron, zirconium, silicon, manganese, aluminium, cerium and mixtures thereof and also modifications in which the oxides are the active agents.

For the purposes of the present invention, it is, however, also advantageous to provide such cosmetic and dermatological preparations whose main purpose is not protection against sunlight, but which nevertheless comprise substances which protect against UV. For example, UV-A and UV-B filter substances are commonly incorporated into day cream.

The preparations according to the invention can advantageously comprise further substances which absorb UV radiation in the UV-B range, the total amount of filter substances being, for example, from 0.1% by weight to 30% by weight, preferably from 0.5 to 15% by weight, based on the total weight of the preparations, in order to provide cosmetic preparations which protect the hair and/or the skin from the whole range of ultraviolet radiation.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3-(4-methylbenzyl-idene)camphor, 3-benzylidenecamphor;

4-aminobenzoic acid derivatives, preferably 2-ethylhexyl 4-(dimethylamino)benzoate, amyl 4-(dimethylamino)benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate;

triazine derivatives symmetrically or unsymmetrically substituted with regard to the $C_3$ axis of the parent triazine substance, preferably tris(2-ethylhexyl) 4,4',4"-(1,3,5-triazine-2,4,6-triyltriimino)trisbenzoate (symmetrical) and 2,4-bis{[4-(2-ethylhexyloxy)-2-hydroxy]phenyl}-6-(4-methoxyphenyl)-1,3,5-triazine, 2,4-bis{[4-(3-sulphonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4bis{[4-(2-ethylhexyloxy)-2-hydroxy}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenlyamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris(trimethyl-siloxysilylpropyloxy)-2-hydroxy]phenyl}-6-(4-methoxyphenyl)-1,3,5-triazine, 2,4-bis{[4-(2"-methylpropenyloxy)-2-hydroxy]phenyl}-6-(4-methoxyphenyl)-1,3,5-triazine, 2,4-bis{[4-(1',1',1',3',5',5',5'-heptamethylsiloxy-2-methylpropyloxy)-2-hydroxy]phenyl}-6-(4-methoxyphenyl)-1,3,5-triazine (unsymmetrical), benzotriazole derivatives, preferably 2,2'-methylenebis(6-(2H-benzotriazol-2-yl)-4-(1,1,3,3-tetramethylbutyl)phenol)

and UV filters bonded to polymers.

Examples of advantageous water-soluble UV-B filter substances are:

salts of 2-phenylbenzimidazole-5-sulphonic acid, such as its sodium, potassium or its triethanolammonium salt, and also the sulphonic acid itself;

sulphonic acid derivatives of 3-benzylidenecamphor, such as e.g. 4-(2-oxo-3-bornylidenemethyl)benzenesulphonic acid, 2-methyl-5-(2-oxo-3-bornylidene-methyl)sulphonic acid and their salts.

The list of said UV-B filters, which may be used in the Pickering emulsions according to the invention, is of course not intended to be limiting.

It can also be advantageous to use, in the Pickering emulsions according to the invention, UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Further advantageous UV-A filter substances are phenylene-1,4-bis(2-benzimidazyl)-3,3'-5,5'-tetrasulphonic acid:

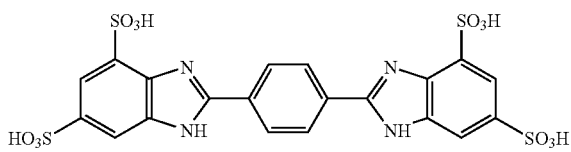

and its salts, particularly the corresponding sodium, potassium or triethanolammonium salts, in particular phenylene-1,4-bis(2-benzimidazyl)-3,3'-5,5'-tetrasulphonic acid bis-sodium salt:

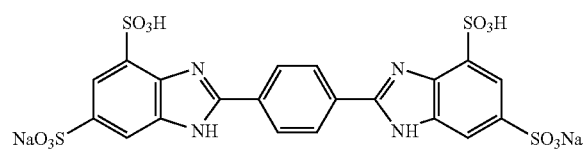

and 1,4-di(2-oxo-10-sulpho-3-bornylidenemethyl)benzene and salts thereof (in particular the corresponding 10-sulphato compounds, in particular the corresponding sodium, potassium or triethanolammonium salt), which is also referred to as benzene-1,4-di(2-oxo-3-bornylidenemethyl-10-sulphonic acid) and is characterized by the following structure:

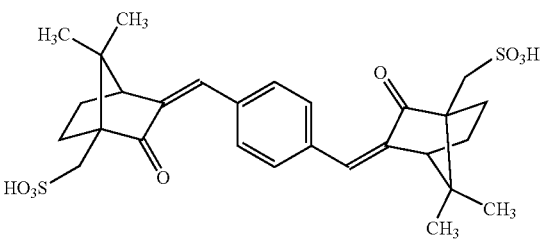

Advantageous UV filter substances are also so-called-broad-band filters, i.e. filter substances which absorb both UV-A and UV-B radiation.

A broad-band filter which is to be used advantageously is, for example, ethylhexyl 2-cyano-3,3-diphenylacrylate (octocrylene), which is obtainable from BASF under the name Uvinul® N 539 and is characterized by the following structure:

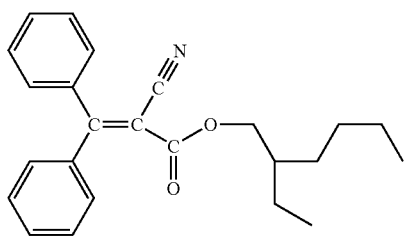

Preparations which contain UV-A filters or so-called broad-band filters are also provided by the invention. The amounts which may be used are as for the UV-B combination.

Preparations according to the invention can also be advantageously used as bases for cosmetic deodorants and antiperspirants, so that a particular embodiment of the present invention relates to Pickering emulsions as bases for cosmetic deodorants.

Cosmetic deodorants are used to control body odour which arises when fresh sweat, which is in itself odourless, is decomposed by microorganisms. Customary cosmetic deodorants are based on various modes of action.

In antiperspirants, astringents, mainly aluminium salts, such as aluminium hydroxychloride (aluchlorhydrate), reduce sweat production.

The use of antimicrobial substances in cosmetic deodorants can reduce the bacterial flora of the skin. In an ideal situation, only the microorganisms which cause the odour should be effectively reduced. The flow of sweat itself is not influenced as a result, and in ideal circumstances, only microbial decomposition of sweat is stopped temporarily.

The combination of astringents and antimicrobial substances in one and the same composition is also common.

All active ingredients common for deodorants or antiperspirants can advantageously be used, for example odour concealers, such as customary perfume constituents, odour absorbers, for example the phyllosilicates described in Laid-Open Patent Specification DE 40 09 347, of these in particular montmorillonite, kaolinite, illite, beidellite, nontronite, saponite, hectorite, bentonite, smectite, and also, for example, zinc salts of ricinoleic acid. Anitbacterial agents are also suitable for incorporation into the W/O emulsion sticks according to the invention. Advantageous substances are, for example, 2,4,4,'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active ingredients or active ingredient combinations described in Patent Laid-Open Specifications DE-37 40 186, DE-39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE-196 02 111, DE-196 31 003, DE-196 31 004 and DE-196 34 019, and in Patent Specifications DE-42 29 737, DE-42 37 081, DE-43 24 219, DE-44 29 467, DE-44 23 410 and DE-195 16 705. Sodium hydrogencarbonate can also be used advantageously.

The list of said active ingredients or active ingredient combinations which can be used in the Pickering emulsions according to the invention is not of course intended to be limiting.

The cosmetic deodorants according to the invention can be present in the form of hydrous, cosmetic preparations which can be applied from normal containers.

The amount of antiperspirant active ingredients or deodorants (one or more compounds) in the preparations is preferably 0.01 to 30% by weight, particularly preferably 0.1–20% by weight, in particular 1–10% by weight, based on the total weight of the preparation.

The sticks according to the invention are also excellent vehicles for dermatological active ingredients. In particular, they are suitable as carriers for substances effective against acne. Acne is a skin disorder of many different forms and causes, characterized by non-inflamed and inflamed bumps, originating from blocked hair follicles (comedones) which can lead to the formation of pustules, abscesses and scars. The most frequent is Acne vulgaris, which occurs mainly in puberty. Causative conditions for Acne vulgaris are the keratinization and blocking of the hair follicle opening, the production of sebum, which is dependent on the level of male sex hormones in the blood, and the production of free fatty acids and tissue-damaging enzymes by bacteria (*Propionibacterium acnes*).

It is therefore advantageous to add to the preparations according to the invention substances effective against acne which are effective, for example, against *Propionibacterium acnes* (for example those described in DE-A 42 29 707, DE-A 43 05 069, DE-A 43 07 976, DE-A 43 37 711, DE-A 43 29 379), but also other substances which are effective against acne, for example all-trans-retinoic acid, 13-cis-retinoic acid and related substances) or antiinflammatory active ingredients, for example batyl alcohol (α-octadecyl glyceryl ether), selachyl alcohol (α-9-octadecenyl glyceryl ether), chimyl alcohol (α-hexadecyl glyceryl ether) and/or bisabolol, and antibiotics and/or keratolytics.

Keratolytics are substances which soften keratinized skin (such as e.g. warts, corns, calluses and the like) so that it can be removed more easily or so that it falls off or peels off.

All of the common substances effective against acne can be used advantageously, in particular benzoyl peroxide, bituminosulphonates (ammonium, sodium and calcium salts of shale oil sulphonic acids), salicylic acid (2-hydroxybenzoic acid), miconazole (1-[2-(2,4-dichlorobenzyloxy)-2-(2,4-dichlorophenyl)ethyl]imidazole) and derivatives, adapalene (6-[3-(1-adamantyl)-4-methoxyphenyl]-2-naphthoic acid), azelaic acid (nonanedioic acid), mesulphene (2,7-dimethylthianthrene, $C_{14}H_{12}S_2$), and aluminium oxide, zinc oxide and/or finely dispersed sulphur.

The amount of antiacne agents (one or more compounds) in the preparations is preferably 0.01 to 30% by weight, particularly preferably 0.1–20% by weight, in particular 1–10% by weight, based on the total weight of the preparation.

The following examples serve to illustrate the present invention, without limiting it. The numerical values in the examples indicate percentages by weight, based on the total weight of the respective preparations.

| | Examples | | | | | |
|---|---|---|---|---|---|---|
| | 1 W/O | 2 W/O | 3 W/O | 4 O/W | 5 O/W | 6 O/W |
| Titanium dioxide (Eusolex T2000) | | 1 | 6 | | | 2 |
| Zinc oxide | | | 4 | | | 4 |
| Silica (Aerosil R972) | | | 0.5 | | | |
| Talc (Talkum Micron) | | 2 | | | | |
| Boron nitride | 5 | 3 | 2 | 5 | 3 | 5 |
| Sodium corn starch n-octenyl succinate | | | | | 1 | 1 |
| Orgasol ® 1002 (Polyamide 6) | | 1 | | | 1 | |
| Caprylic/capric triglyceride | 5 | 5 | 5 | 20 | 20 | 20 |
| Octyldodecanol | 10 | | 5 | 20 | | 15 |
| Mineral oil | 10 | | 5 | 20 | | 20 |
| Butylene glycol caprylate/caprate | | 10 | 10 | | 20 | 7 |
| $C_{12–15}$-alkyl benzoate | 10 | 10 | 10 | 5 | 20 | |
| Methylbenzylidenecamphor | | 3 | | | 4 | |
| Octyltriazone | | 1 | | | 4 | |
| Dibenzoylmethane | | 2 | | | 2 | |
| Preservative | 0.5 | 0.5 | 0.5 | 0.5 | 0.5 | 0.5 |
| Glycerol | 5 | 10 | 3 | 5 | 5 | 5 |
| Phenylbenzimidazolsulphonic acid | | 1 | | | 2 | |
| Carbomer | | | | 0.1 | | |
| NaOH 45% strength solution in water | | 0.3 | | 0.1 | | 0.7 |
| EDTA solution | | 1 | | | 1 | |
| Water | ad 100 | ad 100 | ad 100 | ad 100 | ad 100 | ad 100 |

The invention claimed is:

1. A cosmetic or dermatological preparation, wherein the preparation is an oil-in-water or water-in-oil Pickering emulsion comprising:
    (i) an oil phase,
    (ii) an aqueous phase,
    (iii) amphiphilic boron nitride particles which stabilize the emulsion and are dispersible both in water and in oil, and
    (iv) 0 to 0.5% by weight of one or more emulsifiers.

2. The preparation of claim 1, wherein the preparation further comprises one or more substances selected from cosmetic or pharmaceutical auxiliaries, additives and active ingredients.

3. The preparation of claim 1, wherein the preparation comprises from 0.1% to 30% by weight of (iii), based on a total weight of the preparation.

4. The preparation of claim 1, wherein the boron nitride particles have an average particle diameter of less than 20 μm.

5. The preparation of claim 4, wherein the average particle diameter is less than 15 μm.

6. The preparation of claim 1, wherein the boron nitride particles comprise surface treated boron nitride particles.

7. The preparation of claim 6, wherein the surface treated boron nitride particles comprise boron nitride particles coated with at least one of dimethicone and methicone.

8. The preparation of claim 1, wherein the preparation further comprises one or more pigments.

9. The preparation of claim 8, wherein the one or more pigments are selected from one or more of modified polysaccharides, microfine polymer particles and micronized inorganic pigments.

10. The preparation of claim 8, wherein the preparation comprises one or more micronized inorganic pigments selected from amphiphilic metal oxides.

11. The preparation of claim 10, wherein the amphiphilic metal oxides are selected from titanium dioxide, zinc oxide, iron oxides, mixed iron oxides, silicon dioxide and silicates.

12. The preparation of claim 8, wherein the one or more pigments have an average particle diameter of from 1 nm to 200 nm.

13. The preparation of claim 12, wherein the average particle diameter is from 5 nm to 100 nm.

14. The preparation of claim 1, wherein the preparation further comprises one or more antioxidants.

15. The preparation of claim 1, wherein the preparation further comprises one or more UV protectants.

16. The preparation of claim 1, wherein the preparation comprises one or more substances selected from astringents, antimicrobially effective substances and substances effective against acne.

17. The preparation of claim 1, wherein the preparation is an oil-in-water emulsion.

18. The preparation of claim 1, wherein the preparation is a water-in-oil emulsion.

19. A cosmetic or dermatological preparation, wherein the preparation is an oil-in-water or water-in-oil Pickering emulsion which is emulsifier-free and comprises:

(i) an oil phase, (ii) an aqueous phase, and (iii) amphiphilic boron nitride particles which are dispersible both in water and in oil.

20. The preparation of claim 19, wherein the boron nitride particles have an average particle diameter of less than 15 µm.

* * * * *